(12) United States Patent
Amouzadeh Tabrizi et al.

(10) Patent No.: US 11,199,520 B2
(45) Date of Patent: Dec. 14, 2021

(54) ELECTROCHEMICAL CHLORINE GAS SENSOR AND FABRICATION THEREOF

(71) Applicants: Mahmoud Amouzadeh Tabrizi, Tehran (IR); Mojtaba Shamsipur, Tehran (IR); Reza Saber, Tehran (IR); Saeed Sarkar, Tehran (IR)

(72) Inventors: Mahmoud Amouzadeh Tabrizi, Tehran (IR); Mojtaba Shamsipur, Tehran (IR); Reza Saber, Tehran (IR); Saeed Sarkar, Tehran (IR)

(*) Notice: Subject to any disclaimer, the term of this patent is extended or adjusted under 35 U.S.C. 154(b) by 0 days.

(21) Appl. No.: 15/641,184

(22) Filed: Jul. 3, 2017

(65) Prior Publication Data

US 2017/0299542 A1    Oct. 19, 2017

Related U.S. Application Data

(60) Provisional application No. 62/375,910, filed on Aug. 17, 2016.

(51) Int. Cl.
| | | |
|---|---|---|
| *G01N 27/404* | (2006.01) | |
| *G01N 27/30* | (2006.01) | |
| *C25D 3/62* | (2006.01) | |
| *C25D 5/48* | (2006.01) | |
| *G01N 33/00* | (2006.01) | |
| *G01N 27/413* | (2006.01) | |
| *C25D 7/00* | (2006.01) | |

(52) U.S. Cl.
CPC .......... *G01N 27/4045* (2013.01); *C25D 3/62* (2013.01); *C25D 5/48* (2013.01); *C25D 7/00* (2013.01); *G01N 27/301* (2013.01); *G01N 27/413* (2013.01); *G01N 33/0052* (2013.01)

(58) Field of Classification Search
CPC ............ G01N 27/4045; G01N 27/413; G01N 27/301; G01N 33/0052; C25D 7/00; C25D 5/48; C25D 3/62
See application file for complete search history.

(56) References Cited

U.S. PATENT DOCUMENTS

| | | | |
|---|---|---|---|
| 7,422,646 B2 * | 9/2008 | Prohaska | ........... G01N 27/4074 156/60 |
| 7,438,796 B2 | 10/2008 | Salzer | |
| 9,063,079 B2 | 6/2015 | Eckhardt et al. | |
| 2002/0157967 A1 | 10/2002 | Ling et al. | |

(Continued)

FOREIGN PATENT DOCUMENTS

GB    2117121 B    9/1986

OTHER PUBLICATIONS

Virendra V. Sing, International Journal of Electrochemistry, vol. 2012, Nov. 2011 (Year: 2011).*

(Continued)

*Primary Examiner* — Louis J Rufo
(74) *Attorney, Agent, or Firm* — Bajwa IP Law Firm; Haris Zaheer Bajwa (57) ABSTRACT

An electrochemical chlorine gas sensor is disclosed with a working electrode, a counter electrode, and a reference electrode. The working electrode may be coated with a nanoporous gold layer, a first solution comprising an ionic liquid, and a second solution that may be selected from a Nafion solution, a chitosan solution, an agar solution, or combinations thereof. The reference and counter electrodes may be further coated with the ionic liquid.

14 Claims, 9 Drawing Sheets

(56) References Cited

U.S. PATENT DOCUMENTS

| | | | |
|---|---|---|---|
| 2010/0147705 A1 | 6/2010 | Compton et al. | |
| 2010/0307804 A1* | 12/2010 | Oppermann | C22C 1/08 174/258 |
| 2011/0226619 A1* | 9/2011 | Eckhardt | G01N 27/4045 204/417 |

OTHER PUBLICATIONS

State of Understanding of Nation Kenneth A. Mauritz and Robert B. Moore Chemical Reviews 2004 104 (10), 4535-4586 DOI: 10.1021/cr0207123 (Year: 2004).*

PubChem for Nation available at: https://pubchem.ncbi.nlm.nih.gov/compound/Nafion (Year: 2020).*

Nation Technical Bullitin T-01, CHemous Company (Year: 2016).*

Gengzhi Sun, Electrochemical chlorine sensor with multi-walled carbon nanotubes as electrocatalysts, Electrochemistry Communications, Jul. 18, 2007, vol. 9, pp. 2436-2440.

Xing-Jiu Huang, Electroreduction of Chlorine Gas at Platinum Electrodes in Several Room Temperature Ionic Liquids: Evidence of Strong Adsorption on the Electrode Surface Revealed by Unusual Voltammetry in Which Currents Decrease with Increasing Voltage Scan Rates, The Journal of Physical Chemistry C, 2008, vol. 112, Issue 49, p. 19477-19483.

Linhongjia Xiong, Amperometric Gas detection: A Review, International journal of Electrochemical Science, Sep. 29, 2014, vol. 9, pp. 7152-7181.

Mrendra V. Singh, Applications of Ionic Liquids in Electrochemical Sensors and Biosensors, International Journal of Electrochemistry, Nov. 2011, vol. 2012, Article ID 165683, 19 pages.

Marcel A. G. Zevenbergen, Electrochemical Sensing of Ethylene Employing a Thin Ionic-Liquid Layer, Analytical Chemistry, Jul. 1, 2011, vol. 83, pp. 6300-6307.

Zhe Wang, Highly Sensitive Capacitive Gas Sensing at Ionic Liquid-Electrode Interfaces, Analytical Chemistry, Dec. 25, 2015, vol. 88, pp. 1959-1964.

Hongjun Chen, Direct electrochemistry and electrocatalysis of horseradish peroxidase immobilized in Nafion-RTIL composite film, Electrochemistry Communications, Nov. 9, 2006, vol. 9, pp. 469-474.

Sudkate Chaiyo, Electrochemical sensors for the simultaneous determination of zinc, cadmium and lead using a Nafion/ionic liquid/graphene composite modified screen-printed carbon electrode, Analytica Chimica Acta, Mar. 10, 2016, vol. 918, pp. 26-34.

Wei Sun, Electrochemistry and electrocatalysis of hemoglobin in nafion/nano-CaCO3 film on a new ionic liquid BPPF6 modified carbon paste electrode, The Journal of Physical Chemistry B, 2007, vol. 111, Issue 17, pp. 4560-4567.

Wei Sun, Electrochemistry and Electrocatalysis of a Nafion/Nano-CaCO3/Hb Film Modified Carbon Ionic Liquid Electrode Using BMIMPF6 as Binder, Electroanalysis, 2007, vol. 19, No. 13, pp. 1368-1374.

Renyun Zhang, Porous Gold Films—A Short Review on Recent Progress, Materials, 2014, vol. 7, pp. 3834-3854.

"State of Understanding of Nation" by Kenneth A. Mauritz et al., published by Chem. Rev. 2004, 104, 4535-4585.

* cited by examiner

FIG. 1

(Related Art)

ELECTROCHEMICAL CHLORINE GAS SENSOR AND FABRICATION THEREOF

CROSS-REFERENCE TO RELATED APPLICATION

This application claims the benefit of priority from U.S. Provisional Patent Application Ser. No. 62/375,910, filed on Aug. 17, 2016, and entitled "ELECTROCHEMICAL CHLORINE GAS SENSOR AND FABRICATION THEREOF," which is incorporated herein by reference in its entirety.

TECHNICAL FIELD

The present disclosure generally relates to gas sensors, particularly to electrochemical gas sensors, and more particularly to an electrochemical chlorine gas sensor.

BACKGROUND

Chlorine is a diatomic yellow-green gas with high oxidizing potential. The high oxidizing potential of chlorine has led to its use in the development of commercial bleaches and disinfectants, as well as reagents for various processes in chemical industries. Chlorine is also used in the manufacturing of a wide range of consumer products, such as polyvinyl chloride, and intermediates for the production of plastics.

Although it is used widely in industry, chlorine at specified concentrations is extremely dangerous and poisonous for all living organisms. For example, chlorine was used during World War I as the first gaseous chemical warfare agent. Several industrial accidents have also been reported at facilities storing chlorine that resulted in significant economic damages.

Even small amounts of chlorine gas are known to affect the health of human beings. Generally, humans can detect the odor of chlorine gas at ranges from 0.1-0.3 ppm. At higher ranges of 1-3 ppm, there is typically a mild mucus membrane irritation that can usually be tolerated by humans for about an hour. In the range of 5-15 ppm, there is moderate mucus membrane irritation. However, at 30 ppm and beyond, there is immediate chest pain, shortness of breath, and coughing. At higher ranges of approximately 40-60 ppm, a toxic pneumonitis and/or acute pulmonary edema can develop. Concentrations of about 400 ppm and beyond are generally fatal with exposure over 30 minutes, and at 1000 ppm and above, death occurs within only a few minutes.

Thus, the potential dangers and toxicity of chlorine gas can be present even at low concentrations. There is a need in the art for methods and systems to detect chlorine gas at very low concentrations, where such systems have high selectivity and sensitivity, to help prevent health and economic damages.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure is directed to an electrochemical chlorine gas sensor including a working electrode, a counter electrode, and a reference electrode. The working electrode may be coated with a nanoporous gold layer, a first liquid comprising an ionic liquid, and a second solution that may be selected from a Nafion solution, a chitosan solution, an agar solution, or combinations thereof. The reference and counter electrodes may further be coated with the first solution.

The above general aspect may include one or more of the following features. For example, the ionic liquid may be [Emim][PF6] or Cholin acetate. In some implementations, the ionic liquid may be selected from Tris(2-hydroxyethyl) methylammonium methylsulfate, Benzyldimethyltetradecylammonium chloride anhydrous, Tetrahexylammonium hydrogensulfate, or combinations thereof. According to some other implementations, the ionic liquid may be selected from 1-Allyl-3-methylimidazolium bis(trifluoromethylsulfonyl)imide, 1-Benzyl-3-methylimidazolium hexafluorophosphate, 1,3-Bis(cyanomethyl)imidazolium bis(trifluoromethylsulfonyl)imide, 1-Butyl-2,3-dimethylimidazolium tetrafluoroborate, 1-Butyl-3-methylimidazolium methanesulfonate, or combinations thereof. In other implementations, the ionic liquid may be selected from 1-Butyl-3-methylimidazolium acetate, 1-Butyl-3-methylimidazolium hydrogen sulfate, 1-Butyl-3-methylimidazolium tetrafluoroborate, 1,2,3-Trimethylimidazolium methyl sulfate, or combinations thereof. In some implementations, the ionic liquid may be selected from Tetrabutylphosphonium methanesulfonate, Tributylmethylphosphonium methyl sulfate, Trihexyltetradecylphosphonium bis(2,4,4-trimethylpentyl)phosphinate, Trihexyltetradecylphosphonium bis(trifluoromethylsulfonyl)amide, or combinations thereof. According to other implementations, the ionic liquid may be selected from 1-Butyl-3-methylpyridinium bis(trifluormethylsulfonyl)imide, 1-Butyl-4-methylpyridinium chloride, 1-Butyl-4-methylpyridinium hexafluorophosphate, 3-Methyl-1-propylpyridinium bis(trifluormethylsulfonyl) imide, or combinations thereof. Furthermore, in some implementations, the ionic liquid may be selected from 1-Butyl-1-methylpyrrolidinium bis(trifluoromethylsulfonyl)imide, 1-Butyl-1-methylpyrrolidinium bis(trifluoromethylsulfonyl) imide, 1-Butyl-1-methylpyrrolidinium hexafluorophosphate, 1-Butyl-1-methylpyrrolidinium trifluoromethanesulfonate, or combinations thereof. In another example, the ionic liquid may be Triethylsulfonium bis(trifluoromethylsulfonyl)imide or may be selected from 1-Butyl-1-methylpiperidinium tetrafluoroborate, 1-Butyl-1-methylpiperidinium tetrafluoroborate, 1-Butyl-1-methylpiperidinium bis(trifluoromethylsulfonyl)imide, 1-Butyl-1-methylpiperidinium hexafluorophosphate, 4-Ethyl-4-methylmorpholinium methyl carbonate solution ~50% in methanol:water, 1,2,3-Tris(diethylamino)cyclopropenylium bis(trifluoromethanesulfonyl)imide, 1,2,3-Tris(diethylamino)cyclopropenylium dicyanamide, or combinations thereof.

In another general aspect, the present disclosure is directed to a method of fabricating an electrochemical chlorine gas sensor with a working electrode. The method can include a first step of electrodepositing an alloy film of gold and silver onto a surface of the working electrode to obtain an Ag/Au-coated electrode, and a second step of removing the silver from the alloy film to obtain a nanoporous gold film on the surface of the working electrode. A third step includes coating the nanoporous gold film with an ionic liquid layer to obtain an ionic liquid-modified (IL-modified) working electrode, and a fourth step of coating the IL-modified working electrode with a layer of Nafion to obtain a Nafion-IL/nanoporous gold coated working electrode.

The above general aspect may include one or more of the following features. In one example, electrodepositing the alloy film of gold and silver onto the surface of the working electrode further includes placing the working electrode in an electrochemical cell for use as a cathode electrode, where the electrochemical cell comprises an anode electrode, the cathode electrode, and an electrolyte solution, and applying a voltage between the anode electrode and the cathode electrode for a predetermined amount of time, wherein the electrolyte solution includes a silver salt, a gold salt, and an inert electrolyte. In some cases, the voltage may be between about −250 mV and about −750 mV. In one implementation, the predetermined amount of time may be between about 300 seconds and about 600 seconds, and/or the silver salt may be $AgNO_3$. According to some implementations, the gold salt may be selected from $NaAuCl4$, $HAuCl4$, or combinations thereof. According to other implementations, the inert electrolyte may be selected from NaNO3, Na2SO4, or combinations thereof. According to one implementation, removing the silver from the alloy film may further include washing the Ag/Au-coated electrode with a solvent, where the solvent may be hydrogen peroxide, nitric acid, or combinations thereof. According to another implementation, the solvent may be a nitric acid solution with a concentration of at most 1 M. According to yet another implementation, the solvent may be a hydrogen peroxide solution with a concentration of between 2.5 M and 5 M. In some implementations, coating the nanoporous gold film with an ionic liquid layer may further include drop-casting a first solution comprising ionic liquid onto the nanoporous gold film; and heating the drop-casted first solution to obtain a uniform ionic liquid layer on the nanoporous gold film. In some cases, heating the drop-casted first solution includes heating the drop-casted first solution to a temperature above the melting point of the ionic liquid. In addition, according to some implementations, coating the IL-modified working electrode with a layer of Nafion may further include drop-casting a solution of nNfion in a solvent onto the IL-modified working electrode, and heating the drop-casted solution of nafion to remove the solvent. In one implementation, the solution of Nafion may have a concentration of between 0.5 vol % and 2.5 vol %.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

Generally, electrochemical gas detection sensors are gas detectors that are configured to measure the concentration of a target gas by oxidizing or reducing the target gas at an electrode and measuring the resulting current. For example, in FIG. 1, a schematic representation of an electrochemical gas detection sensor ("sensor") 100 is depicted. In different implementations, electrochemical gas detection sensors may typically include a working electrode 101, a reference electrode 102, a counter electrode 103, and an electrolyte solution 104.

Figure 1:
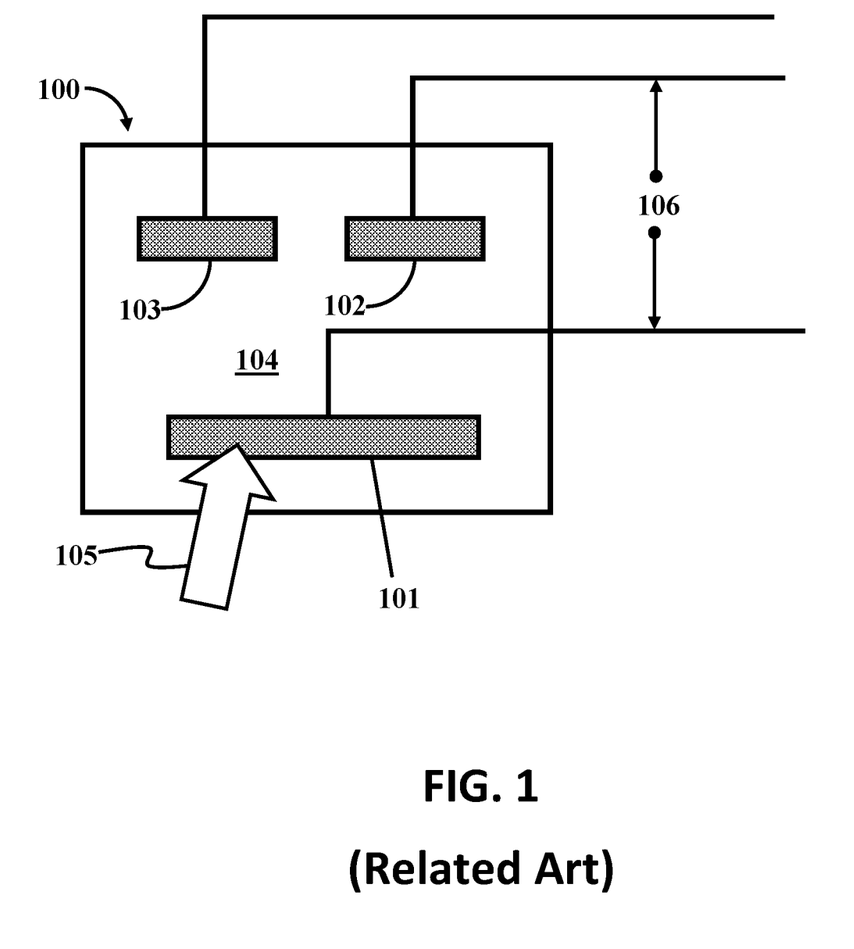
FIG. 1 illustrates a schematic representation of an electrochemical gas detection sensor.

As illustrated schematically in FIG. 1, once a target gas 105 reaches the sensor 100, it undergoes an electrochemical reaction. The electrons involved in the electrochemical reaction can flow from the working electrode 101 through the external circuit, producing an output signal 106 for the sensor. The reference electrode 102 may help provide a stable electrochemical potential in the electrolyte solution 104. The counter-electrode 103 can be configured to complete the circuit of the electrochemical gas detection sensor. The counter electrode 103 may function as a second half-cell, and can allow electrons to enter or leave the electrolyte solution 104.

The present disclosure is directed to a novel electrochemical chlorine gas sensor that comprises a Nafion-IL/nanoporous gold electrode for detecting the presence of chlorine gas. In different implementations, this chlorine gas sensor includes provisions to detect chlorine at very low concentrations. In addition to the components comprising sensor 100 described above with reference to FIG. 1, in some implementations of the present electrochemical chlorine gas sensor, the working electrode may be made of a conductive material (for example, carbon or other conductive materials), and may further be coated with a nanoporous gold layer, a solidified ionic liquid layer, and/or a layer of for example Nafion. In addition, in some implementations, the reference electrode and the counter electrode may be coated with a solidified ionic liquid layer. Benefits from these features include, but are not limited to providing a simple and sensitive electrochemical chlorine gas sensor that may be capable of detecting the presence of chlorine gas even at very low concentrations.

Fabrication of a Novel Electrochemical Chlorine Gas Sensor

Figure 2:
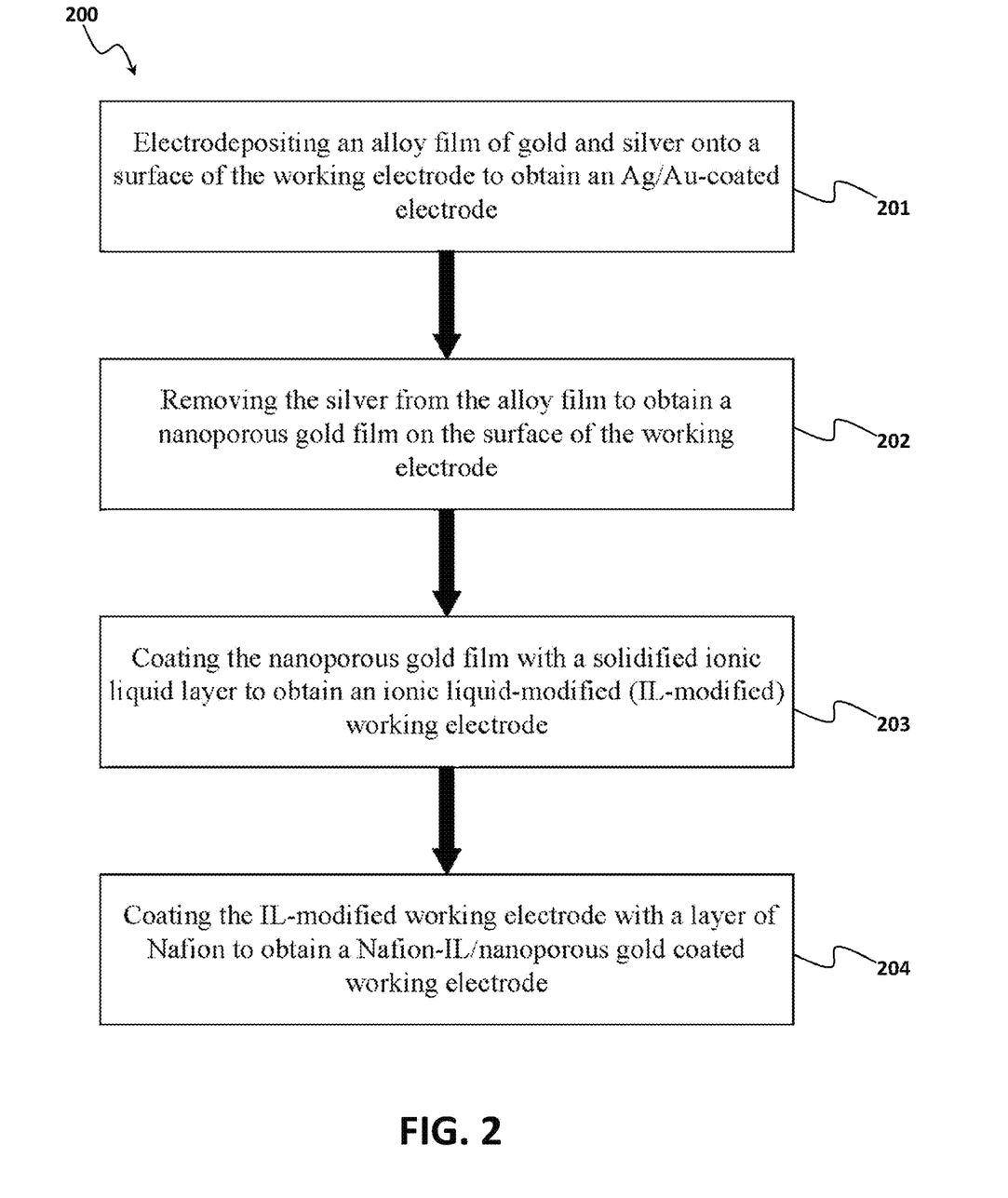
FIG. 2 illustrates a flowchart of a method for fabricating a chlorine sensor, according to one or more implementations of the present disclosure.

For purposes of clarity, FIG. 2 illustrates a method 200 of fabricating an electrochemical chlorine gas sensor according to one or more implementations of the present disclosure. As shown in FIG. 2, in one implementation, the method 200 includes a first step 201 of electrodepositing an alloy film of gold and silver onto a surface of a working electrode to obtain an Ag/Au-coated electrode. A second step 202 can involve removing the silver from the alloy film to obtain a nanoporous gold film on the surface of the working electrode. In a third step 203, the nanoporous gold film can be coated with an ionic liquid layer to obtain an ionic liquid-modified (IL-modified) working electrode. A fourth step 204 may include coating the IL-modified working electrode with a layer of Nafion to obtain a Nafion-IL/nanoporous gold coated working electrode.

Further details regarding the method of fabrication are provided herein. In some implementations, first step 201 may involve washing the working electrode with water and providing the washed electrode as a cathode electrode in an electrochemical cell. In one implementation, the electrochemical cell may further include an anode electrode and an electrolyte solution. In some implementations, the electrolyte solution of the electrochemical cell may include a silver salt, for example $AgNO_3$; a gold salt, which may be selected from $NaAuCl_4$, $HAuCl_4$, or combinations thereof; and/or an inert electrolyte, for example an $NaNO_3$ solution, an $Na_2SO_4$ solution, or combinations thereof.

In different implementations, by applying a predetermined voltage between the anode and cathode electrodes for a predetermined amount of time, a thin film of silver and gold may be coated on the working electrode to obtain an Ag/Au-coated working electrode. In some exemplary implementations, the predetermined voltage can range from −250 mV to −750 mV; however, in other implementations, the predetermined voltage can range from −200 mV to −800 mV. In addition, in some exemplary implementations, the predetermined amount of time can range from 300 s to 600 s, while in other implementations, the predetermined amount of time can range from 100 s to 800 s.

Referring to second step 202, in one implementation, the Ag/Au-coated working electrode may be washed with a solvent. For example, a hydrogen peroxide solution with a molarity of 2.5M to 5M, or a nitric acid solution with a molarity of at most 1M, can be used to remove the silver from the alloy film and obtain a nanoporous gold film on the surface of the working electrode.

With reference to third step 203, in some implementations, a first solution comprising an ionic liquid may be casted onto the working electrode that is coated with a layer of nanoporous gold. In one implementation, the casting may be performed by drop-casting the ionic liquid onto the working electrode. Moreover, in some implementations, the reference electrodes and/or counter electrodes may further be coated with the ionic liquid layer as well. In one implementation, the drop-casted ionic liquid (IL) solution may be heated in order to obtain a uniform ionic liquid layer for coating on the electrodes (such ionic liquid coated electrodes will be hereinafter referred to as IL-modified electrodes).

According to some implementations, the ionic liquid may be for example an ammonium based ionic liquid, such as Tris(2-hydroxyethyl)methylammonium methylsulfate, Benzyldimethyltetradecylammonium chloride anhydrous, Tetrahexylammonium hydrogensulfate; a Choline based ionic liquid, such as Choline acetate; an Imidazolium based ionic liquid, such as 1-Allyl-3-methylimidazolium bis(trifluoromethylsulfonyl)imide, 1-Benzyl-3-methylimidazolium hexafluorophosphate, 1,3-Bis(cyanomethyl)imidazolium bis(trifluoromethylsulfonyl)imide, 1-Butyl-2,3-dimethylimidazolium tetrafluoroborate, 1-Butyl-3-methylimidazolium methanesulfonate; a Basionics based ionic liquid, such as 1-Butyl-3-methylimidazolium acetate, 1-Butyl-3-methylimidazolium hydrogen sulfate, 1-Butyl-3-methylimidazolium tetrafluoroborate, 1,2,3-Trimethylimidazolium methyl sulfate; a Phosphonium based ionic liquid such as Tetrabutylphosphonium methanesulfonate, Tributylmethylphosphonium methyl sulfate, Trihexyltetradecylphosphonium bis(2,4,4-trimethylpentyl)phosphinate, Trihexyltetradecylphosphonium bis(trifluoromethylsulfonyl)amide; a Pyridinium based ionic liquid, such as 1-Butyl-3-methylpyridinium bis(trifluormethylsulfonyl)imide, 1-Butyl-4-methylpyridinium chloride, 1-Butyl-4-methylpyridinium hexafluorophosphate, 3-Methyl-1-propylpyridinium bis(trifluormethylsulfonyl)imide; a Pyrrolidinium based ionic liquid, such as 1-Butyl-1-methylpyrrolidinium bis(trifluoromethylsulfonyl)imide, 1-Butyl-1-methylpyrrolidinium bis(trifluoromethylsulfonyl)imide, 1-Butyl-1-methylpyrrolidinium hexafluorophosphate, 1-Butyl-1-methylpyrrolidinium trifluoromethanesulfonate; a sulfonium based ionic liquid, such as Triethylsulfonium bis(trifluoromethylsulfonyl)imide; or other ionic liquids, such as 1-Butyl-1-methylpiperidinium tetrafluoroborate, 1-Butyl-1-methylpiperidinium bis(trifluoromethylsulfonyl)imide, 1-Butyl-1-methylpiperidinium hexafluorophosphate, 4-Ethyl-4-methylmorpholinium methyl carbonate solution ~50% in methanol water, 1,2,3-Tris(diethylamino)cyclopropenylium bis(trifluoromethanesulfonyl)imide, 1,2,3-Tris(diethylamino)cyclopropenylium dicyanamide, [Emim][PF6], or combinations thereof.

Furthermore, referring to FIG. 2, in some implementations, fourth step 204 may involve coating the IL-modified working electrode with a second solution. In some implementations, the second solution may be a nafion solution, a chitosan solution, an agar solution, or combinations thereof. In different implementations, in order to coat the IL-modified working electrode with the second solution, a solution of (for example, Nafion) with a concentration of for example between 0.5 vol % and 2.5 vol % in a suitable solvent may first be drop-casted onto the IL-modified working electrode. The drop-casted solution may then be heated to remove the solvent and obtain a Nafion-IL/nanoporous gold-coated working electrode.

Example 1: Fabrication of a Modified Electrochemical Chlorine Sensor

For purposes of clarity, one example is provided in which an electrochemical chlorine gas sensor is fabricated pursuant to the teachings of the present disclosure. However, it should be understood that in other implementations, one or more of the steps disclosed herein can be omitted as desired, or additional steps may be included. As described above, in one implementation, the electrochemical gas sensor includes a reference electrode, a working electrode, and a counter electrode. Furthermore, the working electrode may be coated with a layer of nanoporous gold. The working electrode is washed thoroughly with water and then disposed in an electrochemical cell for use as a cathode electrode. In one implementation, a solution comprising approximately 5 mM $NaAuCl_4$ solution, approximately 0.5 mM $AgNO_3$ solution, and approximately 0.5M $NaNO_3$ solution is used as the electrolyte solution in the electrochemical cell. In addition, a voltage of approximately −500 mV potential is then applied for approximately 600 seconds to the electrochemical cell. In some implementations, the working electrode may be coated with a thin film of silver and gold as the electrochemical reaction occurs in the electrochemical cell, thereby producing an Ag/Au-coated working electrode.

In some implementations, the Ag/Au-coated electrode is immersed in an approximately 5M hydrogen peroxide solution for about 12 hours to remove the silver from the alloy film and obtain a nanoporous gold film on the surface of the working electrode. The nanoporous gold film may then be washed thoroughly with water.

In some implementations, the nanoporous gold film coated working electrode, the counter electrode, and the reference electrode are each coated with an ionic liquid layer. To this end, in one implementation, approximately 0.2 g of [Emim][$PF_6$] is drop-casted on the electrode surface and heated to a temperature above the melting point of the ionic liquid (58-62° C.). This process melts the [Emim][$PF_6$] and produces a substantially uniform ionic liquid layer on the electrode surfaces, hereinafter referred to as the IL-modified electrodes.

In some implementations, the IL-modified working electrode is further coated with a Nafion layer to obtain a Nafion-IL/nanoporous gold coated working electrode. To coat the IL-modified working electrode with a Nafion layer, approximately 10 μL of nafion (1%) is drop-casted onto the IL-modified working electrode. The drop-casted solution may then be heated at approximately 50° C. for around 10 minutes to remove the solvent and obtain a Nafion-IL/nanoporous gold-coated working electrode. The Nafion-IL/nanoporous gold-coated working electrode along with the IL-modified reference and counter electrodes are utilized to form the electrochemical chlorine gas sensor as disclosed herein.

Example 2: Characterization Tests

Figure 3:
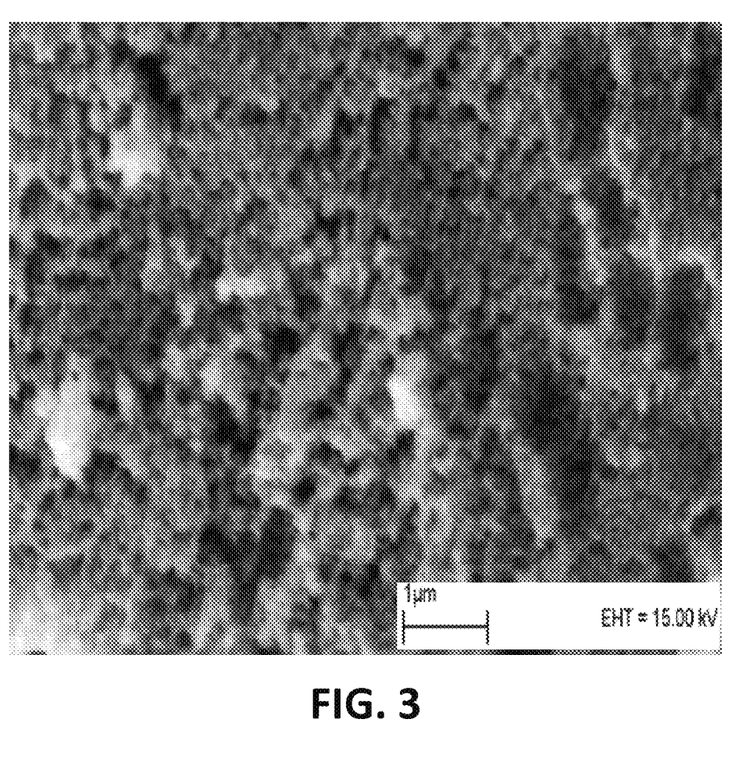
FIG. 3 illustrates a scanning electron microscope (SEM) image of a nanoporous gold-coated working electrode, according to an implementation of the present disclosure.

In this example, the results of some characterization tests performed on the electrochemical chlorine gas sensor fabricated as described in Example 1, are presented. Referring to FIG. 3, a scanning electron microscope (SEM) image of the nanoporous gold-coated working electrode of the electrochemical chlorine sensor is shown. The porous structure of the surface of the nanoporous gold-coated working electrode is visible in FIG. 3, indicating a successful deposition of a nanoporous gold layer onto the surface of the electrode.

Figure 4:
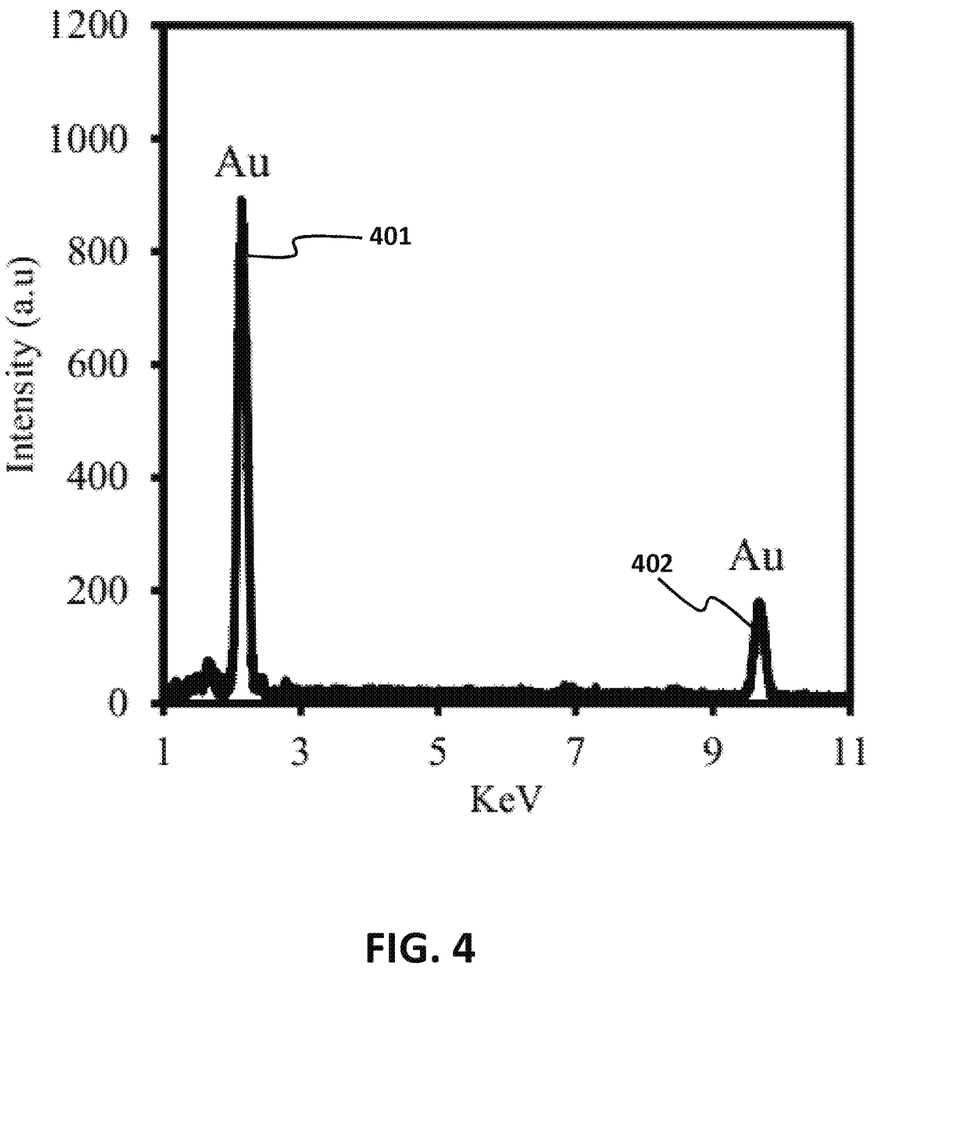
FIG. 4 illustrates an energy-dispersive X-ray (EDX) spectrum of the surface of a nanoporous gold-coated working electrode, according to an implementation of the present disclosure.

In order to obtain a chemical characterization of the surface, an energy dispersive X-ray spectroscopy (EDX) method was used. In FIG. 4 an EDX spectrum of the surface of the nanoporous gold coated working electrode. Referring to FIG. 4, two sharp peaks around 2 keV 401 and 10 keV 402 can be seen in the EDX plot, indicating the existence of the nanoporous gold film on the surface of the working electrode.

Figure 5:
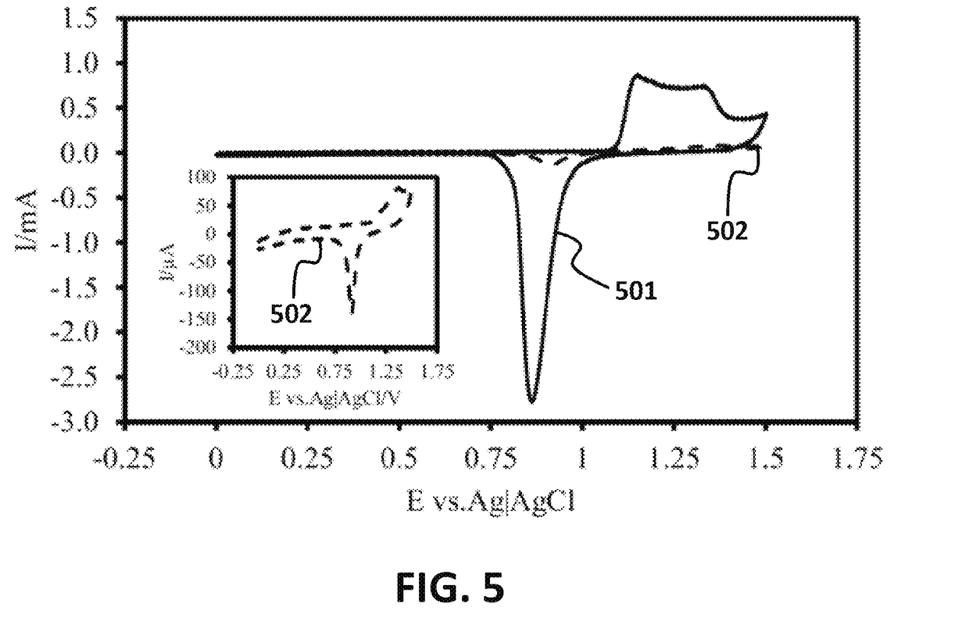
FIG. 5 illustrates cyclic voltammograms of a gold-based screen printed electrode and a nanoporous gold film coated working electrode in a 1M $H_2SO_4$ solution, according to an implementation of the present disclosure.

Furthermore, a cyclic voltammetry (CV) test was used to obtain anodic and cathodic densities. FIG. 5 depicts the cyclic voltammogram of a commercial electrode 501 (i.e., a gold-based screen printed electrode where the working electrode is coated with a layer of gold) and a nanoporous gold film-coated working electrode 502 in a 1M $H_2SO_4$ solution. In FIG. 5, the nanoporous gold film-coated working electrode 502 has larger anodic current densities for the formation of Au oxides and cathodic current densities for the reduction of the oxides. In some implementations, this may be attributed to the presence of electro-active sites on the surface of the nanoporous gold film-coated working electrode 502. The roughness factor may be used to express the ratio between the real surface area and the geometrical area of the electrode. By the integration of the charge consumed in the gold oxide reduction, the roughness factor of the nanoporous gold film-coated working electrode is 89.3 and the roughness factor of the commercial electrode is 4.7.

Figure 6:
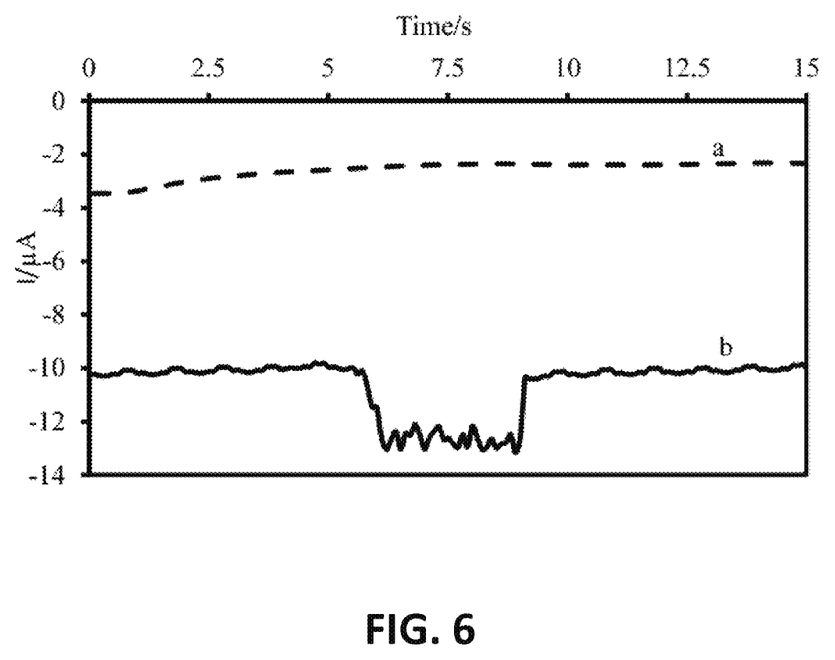
FIG. 6 illustrates the amperometric responses of a Nafion-IL/gold-based screen printed electrode and Nafion-IL/nanoporous gold coated working electrode to 0.01 ppm chlorine gas, according to an implementation of the present disclosure.

Example 3: Electrochemical Behavior of Nafion-IL/Nanoporous Gold Coated Working Electrode FIG. 6 shows the amperometric responses of the Nafion-IL/gold-based screen printed electrode (designated by the letter "a") and the Nafion-IL/nanoporous gold-coated working electrode (designated by the letter "b") to 0.01 ppm chlorine gas. It can be seen that the sensitivity of the Nafion-IL/nanoporous gold-coated working electrode is higher than that of the Nafion-IL/gold-based screen printed electrode. In one implementation, the significantly improved performance of the Nafion-IL/nanoporous gold-coated working electrode may be attributed to the presence of more electroactive sites on the surface of a Nafion-IL/nanoporous gold coated working electrode compared to a gold-based screen printed electrode.

Figure 7:
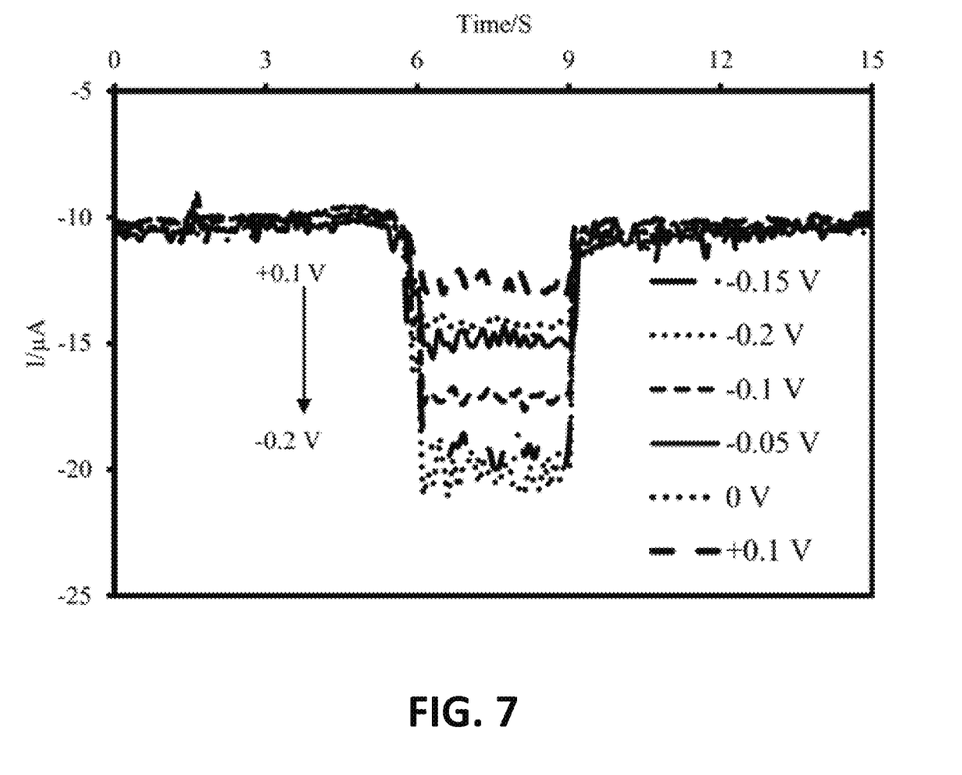
FIG. 7 illustrates a plot of the applied potentials in a range of +0.1V to −0.2V versus the amperometric responses of a gold-based screen printed electrode and a nanoporous gold film coated working electrode to 1.0 ppm chlorine gas, according to an implementation of the present disclosure.

In addition, the effect of applied potentials on the amperometric responses of 1.0 ppm chlorine gas was investigated in a range of +0.1V to −0.2V, and the results are plotted in FIG. 7. As shown in FIG. 7, the sensor response increases rapidly with a decrease in the applied potential from +0.1V to −0.2V, and reaches its maximum at −0.2 V. Therefore, in this case, −0.2 V may be chosen as the optimum detection potential.

Figure 8:
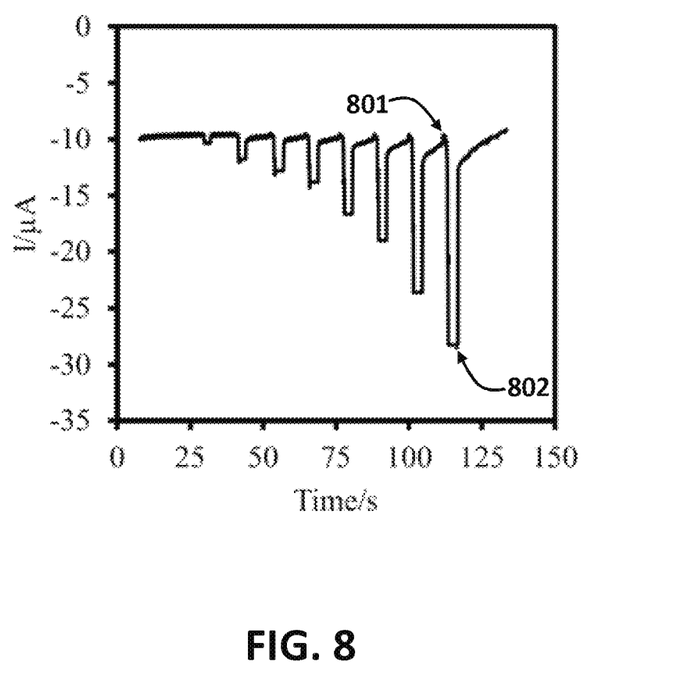
FIG. 8 illustrates a typical current-time plot for a Nafion-IL/nanoporous gold-coated working electrode at various chlorine concentrations, according to an implementation of the present disclosure.

FIG. 8 shows a typical current-time plot of the Nafion-IL/nanoporous gold-coated working electrode for different chlorine gas concentrations at an applied potential of −0.2V. Referring to FIG. 8, once chlorine gas is introduced to the sensor at a point 801, the sensor generates an amperometric response indicating the presence of the chlorine gas. In addition, once the stream of the chlorine gas is cut off at a point 802, the sensor rapidly returns to its reference signal indicating an absence of the chlorine gas.

Figure 9:
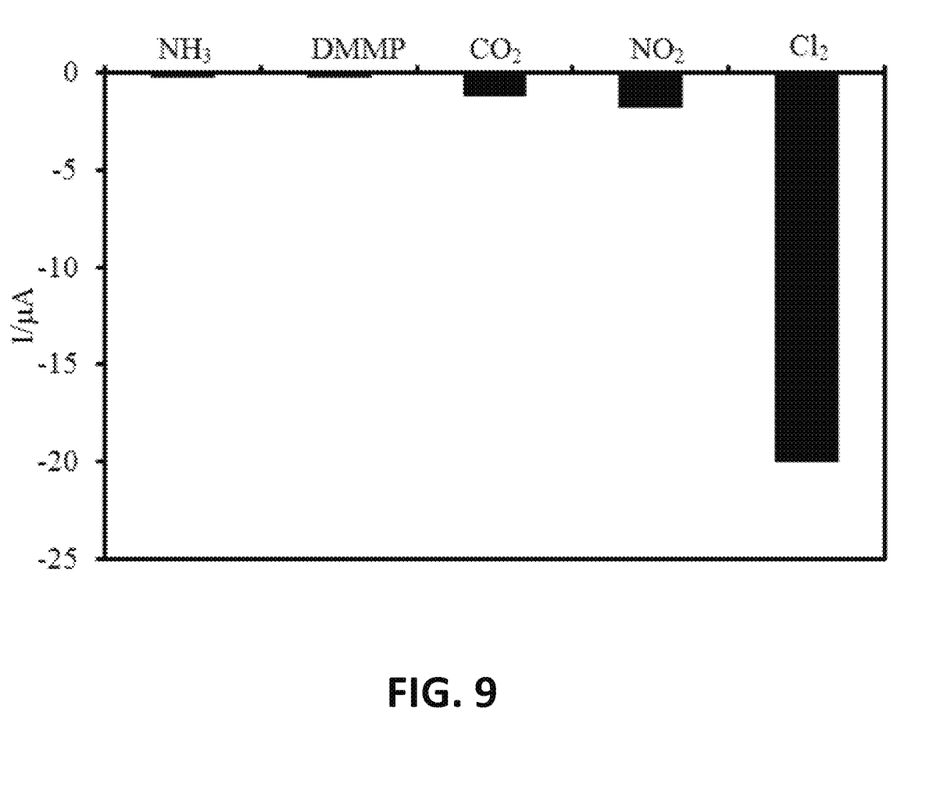
FIG. 9 illustrates a chart of amperometric response of an electrochemical chlorine sensor with a Nafion-IL/nanoporous gold-coated working electrode to different gases with similar concentrations, according to an implementation of the present disclosure.

The effects of interfering compounds were studied on the determination of chlorine gas by the chlorine gas sensor. For example, FIG. 9 shows a chart of amperometric responses of the disclosed electrochemical chlorine sensor to different gases with similar concentrations. In FIG. 9, no interference is observed with ammonia ($NH_3$), dimethyl-methane-phosphonate (DMMP), nitrogen dioxide ($NO_2$) and carbon dioxide ($CO_2$) for 3-fold (1.0 ppm) quantities of chlorine gas.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method of fabricating an electrochemical chlorine gas sensor with a working electrode, the method comprising:
   electrodepositing an alloy film of gold and silver onto a surface of the working electrode to obtain an Ag/Au-coated electrode;
   removing the silver from the alloy film, thereby obtaining a nanoporous gold film on the surface of the working electrode;
   coating the nanoporous gold film with an ionic liquid layer, thereby obtaining an ionic liquid-modified working electrode; and
   coating the ionic liquid-modified working electrode with a layer of Nafion, thereby obtaining a Nafion ionic liquid/nanoporous gold coated working electrode.

2. The method according to claim 1, wherein electrodepositing the alloy film of gold and silver onto the surface of the working electrode further includes:
   placing the working electrode in an electrochemical cell for use as a cathode electrode, the electrochemical cell comprising an anode electrode, the cathode electrode, and an electrolyte solution; and
   applying a voltage between the anode electrode and the cathode electrode for a predetermined amount of time, wherein the electrolyte solution includes a silver salt, a gold salt, and an inert electrolyte.

3. The method according to claim 2, wherein the voltage is between −250 mV and −750 mV.

4. The method according to claim 2, wherein the predetermined amount of time is between 300 seconds and 600 seconds.

5. The method according to claim 2, wherein the silver salt is $AgNO_3$.

6. The method according to claim 2, wherein the gold salt is selected from the group consisting of NaAuCl4, HAuCl4, and combinations thereof.

7. The method according to claim 2, wherein the inert electrolyte is selected from the group consisting of NaNO3, Na2SO4, and combinations thereof.

8. The method according to claim 1, wherein removing the silver from the alloy film further includes washing the Ag/Au-coated electrode with a solvent, wherein the solvent is selected from the group consisting of hydrogen peroxide, nitric acid, and combinations thereof.

9. The method according to claim 8, wherein the solvent is a hydrogen peroxide solution with a concentration between 2.5 M and 5 M.

10. The method according to claim 8, wherein the solvent is a nitric acid solution with a concentration of at most 1 M.

11. The method according to claim 1, wherein coating the nanoporous gold film with an ionic liquid layer further includes:
    drop-casting a first solution comprising ionic liquid onto the nanoporous gold film; and
    heating the drop-casted first solution to obtain a substantially uniform, solidified ionic liquid layer on the nanoporous gold film.

12. The method according to claim 11, wherein heating the drop-casted first solution further includes heating the drop-casted first solution to a temperature above the melting point of the ionic liquid.

13. The method according to claim 1, wherein coating the ionic liquid-modified working electrode with the layer of Nafion further includes:
   drop-casting a second solution comprising Nafion in a solvent onto the ionic liquid-modified working electrode; and
   heating the drop-casted second solution to remove the solvent.

14. The method according to claim 13, wherein the solution of Nafion has a concentration of between 0.5 vol % and 2.5 vol %.

* * * * *